United States Patent
Mohamed et al.

(10) Patent No.: US 11,998,515 B1
(45) Date of Patent: Jun. 4, 2024

(54) ENHANCEMENT OF CURCUMIN PLASMA LEVELS USING EUCALYPTOL CO-ADMINISTRATION

(71) Applicant: KING FAISAL UNIVERSITY, Al-Ahsa (SA)

(72) Inventors: Maged Elsayed Mohamed, Al-Ahsa (SA); Nancy Safwat Younis, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/237,710

(22) Filed: Aug. 24, 2023

Related U.S. Application Data

(62) Division of application No. 18/138,244, filed on Apr. 24, 2023.

(51) Int. Cl.
| | | |
|---|---|---|
| *A61K 31/12* | (2006.01) | |
| *A61K 9/00* | (2006.01) | |
| *A61K 31/352* | (2006.01) | |
| *A61K 47/38* | (2006.01) | |

(52) U.S. Cl.
CPC ............ *A61K 31/12* (2013.01); *A61K 9/0053* (2013.01); *A61K 31/352* (2013.01); *A61K 47/38* (2013.01)

(58) Field of Classification Search
CPC ............................... A61K 31/12; A61K 31/352
See application file for complete search history.

(56) References Cited

U.S. PATENT DOCUMENTS 11,452,768 B2   9/2022   Hacohen et al.

FOREIGN PATENT DOCUMENTS

| JP | 2017502029 A | 1/2017 |
|---|---|---|
| WO | 2022024095 A1 | 2/2022 |
| WO | 2022024096 A1 | 2/2022 |
| WO | 2022024097 A1 | 2/2022 |
| WO | WO 2022/063371 A1 * | 3/2022 |
| WO | 2022091050 A1 | 5/2022 |
| WO | 2022091051 A1 | 5/2022 |
| WO | 2022091061 A1 | 5/2022 |
| WO | 2022165439 A1 | 8/2022 |

OTHER PUBLICATIONS

Gera et al, Nanoformulations of curcumin: an emerging paradigm for improved remedial application, 2017, Oncotarget, vol. 8, No. 39, p. 66680-66698. (Year: 2017).*

Hegde et al, Curcumin Formulations for Better Bioavailability: What We Learned from Clinical Trials Thus far, Mar. 13, 2023, vol. 8, p. 10713-10746. (Year: 2023).*

Le, Drug Bioavailability, 2022, Merck Manual Professional Version, p. 1-4. (Year: 2022).*

Kurita, Novel Curcumin Oral Delivery Systems, 2013, Anticancer research, vol. 33, p. 2807-2822. (Year: 2013).*

Nikolic, I. et al., "Microstructure and biopharmaceutical performances of curcumin-loaded low-energy nanoemulsions containing eucalyptol and pinene: Terpenes' role overcome penetration enhancement effect?," Eur. J. Pharm. Sci. 142:105135; Jan. 15, 2020.

Yallapu, M. et al., "Curcumin nanoformulations: a future nanomedicine for cancer," Drug Discov. Today 17(1-2): pp. 71-80 (2012).

* cited by examiner

*Primary Examiner* — Samantha L Shterengarts
*Assistant Examiner* — Karen Cheng
(74) *Attorney, Agent, or Firm* — Nath, Goldberg & Meyer; Richard C. Litman

(57) ABSTRACT

Compositions and methods for co-administering curcumin and eucalyptol to a subject. Through the combined administration with eucalyptol, the plasma levels of curcumin will increase over the current baseline, thereby increasing the medicinal activity of the polyphenol and contributing to the reduction of an effective dose thereof, thereby also decreasing the incidence of side effects.

6 Claims, No Drawings

ENHANCEMENT OF CURCUMIN PLASMA LEVELS USING EUCALYPTOL CO-ADMINISTRATION

CROSS-REFERENCE TO RELATED APPLICATION

This application is a divisional of U.S. patent application Ser. No. 18/138,244, filed on Apr. 24, 2023.

BACKGROUND

1. Field

The disclosure of the present patent application relates to compositions and methods for administering curcumin, and particularly to compositions and methods for administering curcumin in combination with eucalyptol.

DESCRIPTION OF THE PRIOR ART

Curcumin, a polyphenol derived from the rhizome of turmeric (*Curcuma longa* L. (Zingiberaceae)) is characterized by a comprehensive range of biological, medicinal, and pharmacological activities. Curcumin has been demonstrated to have antioxidant, antimicrobial, anti-malarial, anticancer, anti-thrombotic, anti-hyperlipidemic, hypoglycemic, anti-inflammatory, anti-rheumatic, and myocardial infarction protective activities. Although it is efficacious and safe, Curcumin has not been widely used as a therapeutic agent, mainly for problems related to its poor bioavailability and solubility. Pharmacokinetic studies of curcumin have exhibited poor absorption, fast metabolism, and fast elimination as major reasons for its poor bioavailability. Several approaches to overcome this problem have been attempted, including using co-administered essential oils e.g., turmeric root oil, or essential oil components e.g., Eugenol. However, none of these approaches has yet achieved a reliable, reproducible solution.

Thus, compositions and methods to solve the aforementioned problems are desired.

Eucalyptol is an oxygenated bicyclic monoterpene, identified in the essential oil of several aromatic plant species, especially belonging to the genus *Eucalyptus*. Eucalyptol is well-known for its pharmacological and medicinal activities, including antibacterial, anti-inflammatory, antihypertensive, and anti-cancer actions.

SUMMARY OF THE INVENTION

The present subject matter relates to the co-administration of doses of curcumin and eucalyptol, which results in the elevation of the plasma concentration of curcumin. This could lead to increased medicinal activity of curcumin and could contribute to the reduction of a specific dose of curcumin needed, thereby decreasing the incidence of possible side effects thereof.

Accordingly, in one embodiment, the present subject matter relates to a composition comprising: curcumin; eucalyptol; and an orally acceptable carrier.

In another embodiment, the present subject matter relates to a method of increasing curcumin plasma levels in a subject, the method comprising: orally administering a composition as described herein to a subject in need thereof, wherein the curcumin and the eucalyptol are co-administered to the subject.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine or pigs, horses, camels, poultry, rabbits, goats, dogs, cats, and the like.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the co-administration of doses of curcumin and eucalyptol, which results in the elevation of the plasma concentration of curcumin. This could lead to increased medicinal activity of curcumin and could contribute to the reduction of a specific dose of curcumin needed, thereby decreasing the incidence of possible side effects thereof.

Accordingly, in one embodiment, the present subject matter relates to a composition comprising: curcumin; eucalyptol; and an orally acceptable carrier.

In an embodiment, the compositions of the present subject matter comprise curcumin and eucalyptol solubilized in 0.5% carboxy methyl cellulose, with saline being used as a carrier.

In another embodiment, the orally acceptable carrier used in the present compositions is saline. In this regard, where saline is used as the orally acceptable carrier, another component should be used to assist in solubilizing the curcumin and the eucalyptol. In a non-limiting embodiment in this regard, the other component used to assist in solubilizing the curcumin and the eucalyptol is carboxy methyl cellulose. Other, similar components useful as solubilization aids are further contemplated herein.

In a further embodiment, the composition comprises about 10 mg/kg of the curcumin. In another embodiment, the composition comprises about 5 to about 20 mg/kg of the eucalyptol.

In an embodiment, the compositions described herein can be prepared by mixing curcumin and eucalyptol with an orally acceptable carrier. For example, the method of making a composition herein can include mixing curcumin and eucalyptol with an orally acceptable carrier with preservatives, buffers, and/or propellants to create the composition. Carriers are inert pharmaceutical excipients, including, but not limited to, binders, suspending agents, lubricants, flavorings, sweeteners, preservatives, dyes, and coatings. In preparing compositions in oral dosage form, any of the carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, sterile parenteral solutions or suspensions, metered aerosol or liquid sprays, drops, ampules, for oral administration. The composition can be presented in a form suitable for daily, weekly, or monthly administration. The compositions herein will contain, per dosage unit, e.g., tablet, capsule, powder, and the like, amounts of the active ingredients necessary to deliver an effective dose. Effective amounts of the curcumin and eucalyptol may be determined initially from the Examples described herein and adjusted for specific targeted diseases using routine methods.

In another embodiment, the present subject matter relates to a method of increasing curcumin plasma levels in a subject, the method comprising: orally administering a composition as described herein to a subject in need thereof, wherein the curcumin and the eucalyptol are co-administered to the subject.

In certain embodiments in this regard, the co-administration of the curcumin and the eucalyptol to the subject elevates plasma concentration of the curcumin in the subject.

In other embodiments, about 10 mg of the curcumin are administered per 1 kg of the subject. Similarly, about 5 to about 20 mg of the eucalyptol can be administered per 1 kg of the subject. In another embodiment, about 10 to about 20 mg of the eucalyptol can be administered per 1 kg of the subject.

Following the co-administration of the curcumin and the eucalyptol orally to the subject, the curcumin plasma levels in the subject can increase by 6-9 times from baseline levels. In this regard, the curcumin plasma level in the subject can exhibit an increase in as short as about 1 hour following oral administration of the present compositions to the subject. Further, the curcumin plasma level in the subject can reach a maximum concentration about 4 hours following oral administration of the compositions to the subject. This means that the curcumin plasma level in the subject can reach a maximum concentration in about 33% less time following oral administration of the composition to the subject when compared to administration of a composition consisting of curcumin only to the subject.

In certain embodiments, the composition can be administered to the subject for at least ten days.

In further embodiments, the present subject matter relates to a method of treating a disease, disorder, or condition in a subject, the method comprising: orally administering a composition as described herein to a subject in need thereof, wherein the curcumin and the eucalyptol are co-administered to the subject.

In certain embodiments in this regard, since the present methods can increase the bioavailability and blood plasma levels of the curcumin following administration, the present methods are applicable to any disease, disorder, or condition treatable by curcumin. Certain non-limiting exemplary diseases, disorders, and conditions in this regard include oxidative and inflammatory conditions, metabolic syndrome, arthritis, anxiety, hyperlipidemia, exercise-induced inflammation and muscle soreness, pain, kidney diseases, inflammatory and degenerative eye conditions, and any combination thereof.

Further contemplated within the present methods are generating an anti-inflammatory and antioxidant effect in a subject receiving the presently described compositions.

In this regard, antioxidant and anti-inflammatory properties are the two primary mechanisms that explain most of the effects of curcumin on the various conditions discussed herein. Curcumin has been shown to improve systemic markers of oxidative stress. There is evidence that it can increase the serum activities of antioxidants such as superoxide dismutase (SOD). Curcumin's effect on free radicals may be carried out by several different mechanisms. It can scavenge different forms of free radicals, such as reactive oxygen and nitrogen species (ROS and RNS, respectively); it can modulate the activity of GSH, catalase, and SOD enzymes active in the neutralization of free radicals; also, it can inhibit ROS-generating enzymes such as lipoxygenase/cyclooxygenase and xanthine hydrogenase/oxidase. In addition, curcumin is a lipophilic compound, which makes it an efficient scavenger of peroxyl radicals, therefore, like vitamin E, curcumin is also considered as a chain-breaking antioxidant.

Oxidative stress has been implicated in many chronic diseases, and its pathological processes are closely related to those of inflammation, in that one can be easily induced by another. In fact, it is known that inflammatory cells liberate several reactive species at the site of inflammation leading to oxidative stress, which demonstrates the relationship between oxidative stress and inflammation. In addition, several reactive oxygen/nitrogen species can initiate an intracellular signaling cascade that enhances pro-inflammatory gene expression. Inflammation has been identified in the development of many chronic diseases and conditions. These diseases include Alzheimer's disease (AD), Parkinson's disease, multiple sclerosis, epilepsy, cerebral injury, cardiovascular disease, metabolic syndrome, cancer, allergy, asthma, bronchitis, colitis, arthritis, renal ischemia, psoriasis, diabetes, obesity, depression, fatigue, and acquired immune deficiency syndrome (AIDS). Tumor necrosis factor α (TNF-α) is a major mediator of inflammation in most diseases, and this effect is regulated by the activation of a transcription factor, nuclear factor (NF)-κB. Whereas TNF-α is said to be the most potent NF-κB activator, the expression of TNF-α is also regulated by NF-κB. In addition to TNF-α, NF-κB is also activated by most inflammatory cytokines; gram-negative bacteria; various disease-causing viruses; environmental pollutants; chemical, physical, mechanical, and psychological stress; high glucose; fatty acids; ultraviolet radiation; cigarette smoke; and other disease-causing factors. Therefore, agents that downregulate NF-κB and NF-κB—regulated gene products have potential efficacy against several of these diseases. Curcumin has been shown to block NF-κB activation increased by several different inflammatory stimuli. Accordingly, the present methods, by virtue of their ability to elevate curcumin blood plasma levels, can treat any of these mentioned conditions.

One such disease associated with inflammation, both chronic and acute, is osteoarthritis (OA), a chronic joint condition. It affects over 250 million people worldwide, leading to increased healthcare costs, impairment in activities of daily living (ADL), and ultimately decreased quality of life. Although OA was once considered primarily a degenerative and non-inflammatory condition, it is now recognized as having inflammatory aspects, including elevated cytokine levels, as well as potentially being connected with systemic inflammation. The administration of curcumin and eucalyptol with OA and rheumatoid arthritis (RA) would be expected to treat such conditions. Regardless of the mechanism by which curcumin elicits its effects, it does appear to be beneficial to several aspects of OA.

The idea that curcumin can attenuate systemic inflammation has implications beyond arthritis, as systemic inflammation has been associated with many conditions affecting many systems. One such condition is Metabolic syndrome (MetS), which includes insulin resistance, hyperglycemia, hypertension, low high-density lipoprotein cholesterol (HDL-C), elevated low-density lipoprotein cholesterol (LDL-C), elevated triglyceride levels, and obesity, especially visceral obesity. The administration of the curcumin and eucalyptol would be expected to attenuate several aspects of MetS, for example, by improving insulin sensitivity, suppressing adipogenesis, and reducing elevated blood pressure, inflammation, and oxidative stress.

In addition, the administration of the curcumin and eucalyptol would be expected to lead to a reduction in plasma triglycerides and cholesterol and elevate HDL-C concentrations.

In other embodiments, the present methods may exert immunomodulatory effects via altering the circulating concentrations of IL-1B, IL-4, and VEGF.

EXAMPLES

Example 1

This experiment involved the use of 6 groups of rats (n=6):

Group 1: is the control group, where the animals received a solution of 0.5% carboxy methyl cellulose (CMC) in normal saline (formulation vehicle) once daily orally for ten days.

Group 2: Rats were given Eucalyptol (20 mg/kg) solubilized in 0.5% carboxy methyl cellulose (CMC) in normal saline once a day orally for ten days.

Group 3: Rats were administered curcumin (10 mg/kg) solubilized in 0.5% carboxy methyl cellulose (CMC) in normal saline once daily orally for ten days.

Groups 4, 5 and 6: Rats were given combinations of curcumin (10 mg/kg) with Eucalyptol (5 mg/kg, group 4), (10 mg/kg group 5), and (20 mg/kg, group 6), solubilized in 0.5% carboxy methyl cellulose (CMC) in normal saline orally once daily for ten days.

After the last dose on day 10, blood samples were withdrawn from animals after 0.5, 1, 2, 4, 6, 12 and 24 hours, and HPLC/DAD techniques determined the concentrations of curcumin.

Results: The results demonstrated the elevation of curcumin concentration in the serum by nearly 7 and 9 fold (when eucalyptol 10 and 20 mg/kg were combined with curcumin, i.e., groups 5 and 6, respectively), relative to the curcumin group (group 3). The curcumin concentration increased in serum after 1 hour of administration and reached the maximum concentration after 4 hours (with eucalyptol 20 mg/kg, group 6) and 6 hours (curcumin alone, group 3). Curcumin concentration decreased (at a lesser rate) when eucalyptol (20 mg/kg) was used after 12 hours.

It is to be understood that the compositions and methods for administering curcumin in combination with eucalyptol are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of increasing curcumin plasma levels in a subject, the method comprising:
   orally administering a composition to a subject in need thereof, wherein the composition comprises:
   about 10 mg of curcumin per kg of body weight in a subject to which the composition is administered;
   about 5 mg to about 20 mg of eucalyptol per kg of body weight in the subject to which the composition is administered; and
   an orally acceptable carrier that is saline;
   wherein the curcumin and the eucalyptol are solubilized in carboxy methyl cellulose; and
   wherein the curcumin and the eucalyptol are co-administered to the subject, wherein the curcumin plasma levels in the subject increased by 6-9 times from baseline plasma levels of curcumin in a subject who is untreated with the composition following oral administration of the composition to the subject.

2. The method of claim 1, wherein about 10 to about 20 mg of the eucalyptol are administered per 1 kg of body weight of the subject.

3. The method of claim 1, wherein the curcumin plasma level in the subject increases about 1 hour following oral administration of the composition to the subject.

4. The method of claim 1, wherein the curcumin plasma level in the subject reaches a maximum concentration about 4 hours following oral administration of the composition to the subject.

5. The method of claim 1, wherein the curcumin plasma level in the subject reaches a maximum concentration in about 33% less time following oral administration of the composition to the subject when compared to administration of a composition consisting of curcumin to the subject.

6. The method of claim 1, wherein the composition is administered to the subject for at least ten days.

\* \* \* \* \*